US00PP21548P3

(12) United States Plant Patent
Madsen

(10) Patent No.: US PP21,548 P3
(45) Date of Patent: Nov. 30, 2010

(54) ***RHIPSALIDOPSIS* PLANT NAMED 'PKMRH01'**

(50) Latin Name: *Rhipsalidopsis×hybrida*
Varietal Denomination: PKMRH01

(75) Inventor: Christian Hald Madsen, Korsor (DK)

(73) Assignee: Gartneriet Pkm A/S, Odense N (DK)

( * ) Notice: Subject to any disclaimer, the term of this patent is extended or adjusted under 35 U.S.C. 154(b) by 12 days.

(21) Appl. No.: 12/453,155

(22) Filed: Apr. 30, 2009

(65) Prior Publication Data

US 2010/0281591 P1 Nov. 4, 2010

(51) Int. Cl.
*A01H 5/00* (2006.01)

(52) U.S. Cl. ..... Plt./372

(58) Field of Classification Search ..... Plt./372
See application file for complete search history.

*Primary Examiner*—Kent L Bell
(74) *Attorney, Agent, or Firm*—Foley & Lardner LLP

(57) ABSTRACT

A new and distinct *Rhipsalidopsis* plant named 'PKMRH01' particularly characterized by its large upright to vertical flowers which are white in color; bi-colored buds which are white and red-purple in color; freely branching growth habit; and ovoid to lanceolatoid in shape buds.

7 Drawing Sheets

Latin name of the genus and species of the plant claimed: *Rhipsalidopsis×hybrida.*

Variety denomination: 'PKMRH01'.

BACKGROUND OF THE INVENTION

The present invention relates to a new and distinct cultivar of *Rhipsalidopsis* plant, botanically known as *Rhipsalidopsis×hybrida*, sometimes referred to as *Rhipsalidopsis* Britton Et Rose, including *Epiphylopsis* Berger, commonly known as either Easter Cactus or Spring Cactus, and hereinafter referred to by the cultivar name 'PKMRH01'.

The new *Rhipsalidopsis* cultivar is a product of a controlled breeding program conducted by the inventor, Christian Hald Madsen, in Søhus, Denmark. The objective of the breeding program was to develop a new *Rhipsalidopsis* cultivar with compact, freely branching habit and unique colored flowers.

The new *Rhipsalidopsis* cultivar originated from a cross made by the inventor in 2005 in Søhus, Denmark. The female or seed parent is the *Rhipsalidopsis×hybrida* cultivar designated Cebemma (U.S. Plant Pat. No. 14,588, European Union, Community Plant Variety Office Grant no.: 13,964). The male or pollen parent is the *Rhipsalidopsis×hybrida* cultivar designated '7302M' (unpatented). The new *Rhipsalidopsis* cultivar was discovered and selected by the inventor as a single flowering plant within the progeny of the stated cross in a controlled environment in 2007 in Søhus, Denmark. The inventor selected 'PKMRH01' on the basis of its bud and flower color, upright, plant habit and freely branching habit.

Asexual reproduction of the new *Rhipsalidopsis* cultivar by phylloclade cuttings was first performed May of 2007 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMRH01' which in combination distinguish this *Rhipsalidopsis* as a new and distinct cultivar:

1. Large upright to vertical flowers which are white in color;
2. Bi-colored buds which are white and red-purple in color;
3. Freely branching growth habit; and
4. Ovoid to lanceolatoid in shape buds.

Plants of the instant cultivar 'PKMRH01' differ primarily from plants of the parental cultivars, Cebemma (female or seed parent; patented, US Plant Pat. No. 14,588, European Union-Community Plant Variety Office Grant no.: 13,964) and '7302M' (male or pollen parent, unpatented) by the following characteristics:

1. Plants of 'PKMRH01' have bi-colored buds which are white, closest to RHS NN155D, and red-purple, closest to RHS 62B, whereas plants of the parental cultivars have one-colored buds, which are white, closest to RHS NN155A, for Cebemma and red-purple, closest to RHS 68A, for '7302M';
2. Plants of 'PKMRH01' produce flowers which are white in color, closest to RHS NN155D, whereas plants of the parental cultivars produce flowers which are white in color, closest to RHS NN155A, for Cebemma and red-purple, closest to RHS 68A, for '7302M'.

The most similar commercial cultivar to the instant cultivar 'PKMRH01' is the female or seed, parental cultivar *Rhipsalidopsis* Cebemma. Plants of the instant cultivar 'PKMRH01' differ primarily from plants of Cebemma as described above.

BRIEF DESCRIPTION OF THE PHOTOGRAPHS

The accompanying photographs illustrate the overall appearance of the new *Rhipsalidopsis* cultivar 'PKMRH01' showing the colors as true as is reasonably possible with colored reproductions of this type. Colors in the photographs may differ slightly from the color values cited in the detailed botanical description, which accurately describe the color of 'PKMRH01'.

DETAILED BOTANICAL DESCRIPTION

Figure 1:
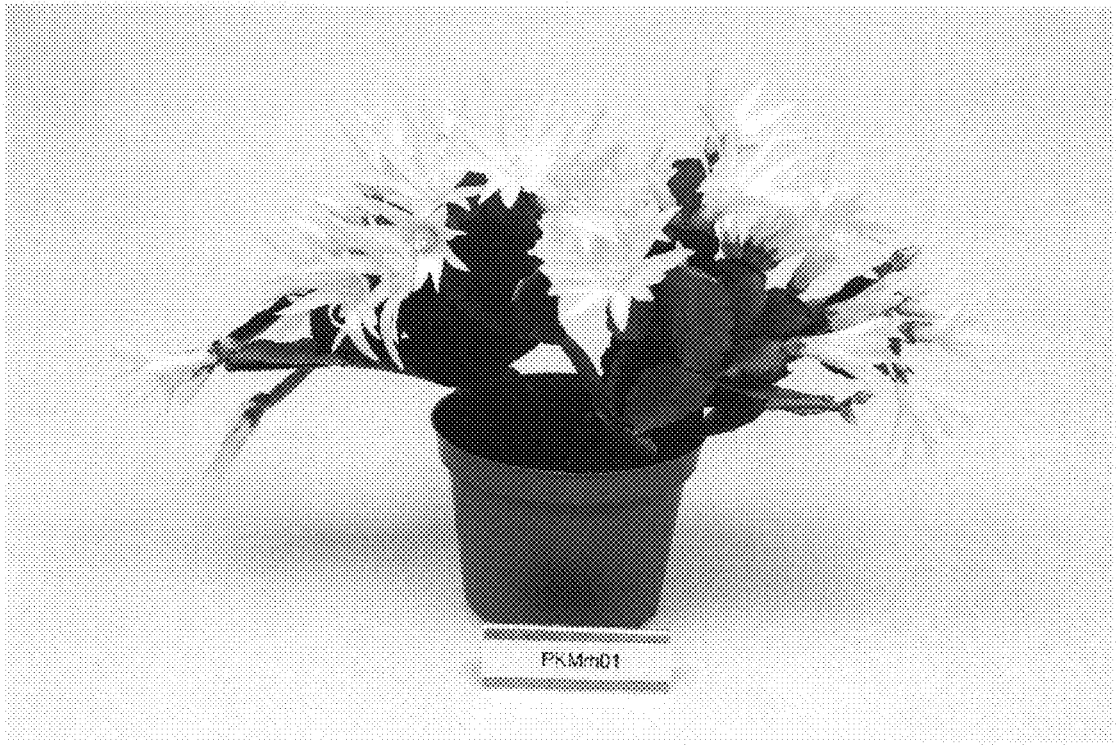
FIG. 1 shows a side perspective view of a typical mature flowering plant of 'PKMRH01' grown in a 9.0 cm pots, at 12 months of age.
Figure 2:
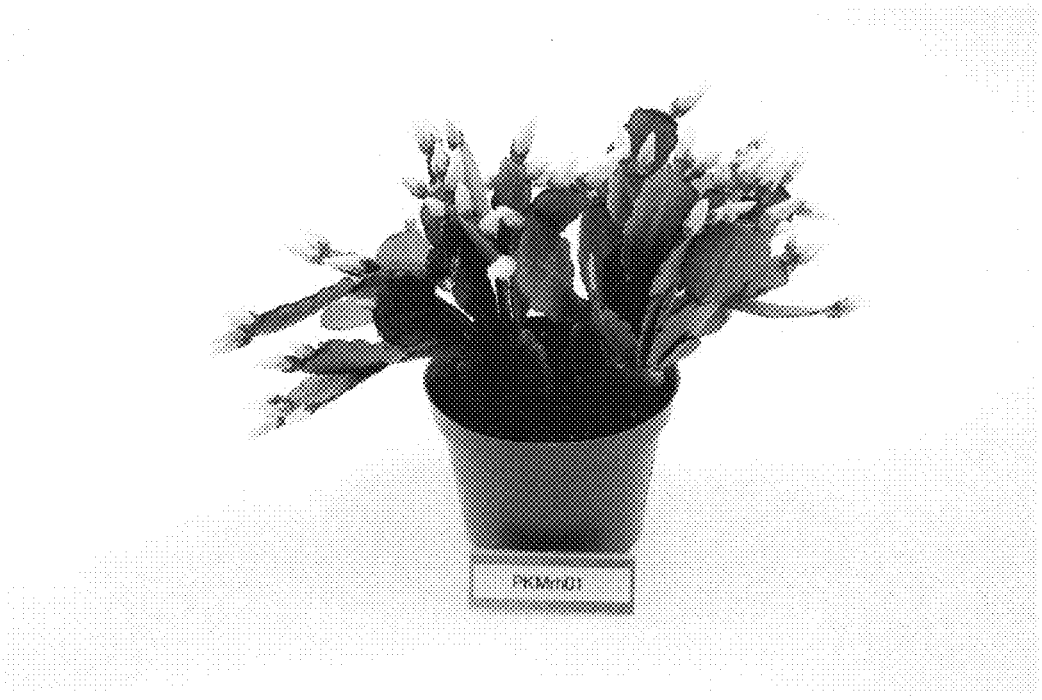
FIG. 2 shows a side perspective view of a typical mature plant of 'PKMRH01' with buds prior to flowering, grown in a 9.0 cm pots, at 11 months of age.
Figure 3:
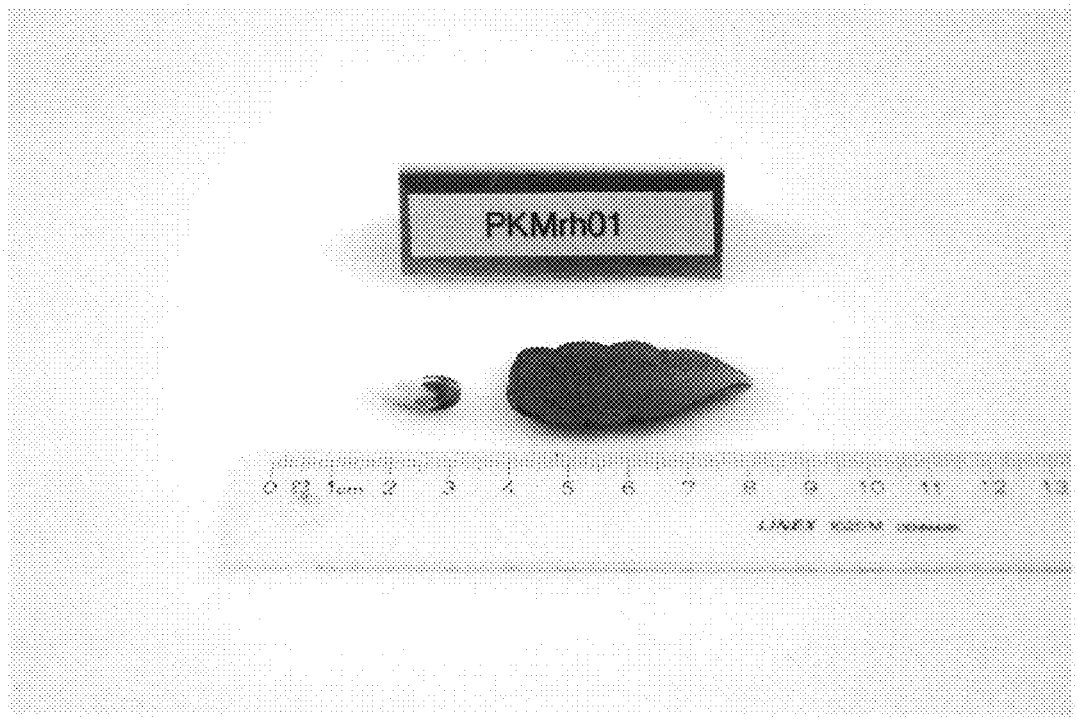
FIG. 3 shows a close-up perspective view of a typical bud just prior to flowering and a typical mature phylloclade of 'PKMRH01'.
Figure 4:
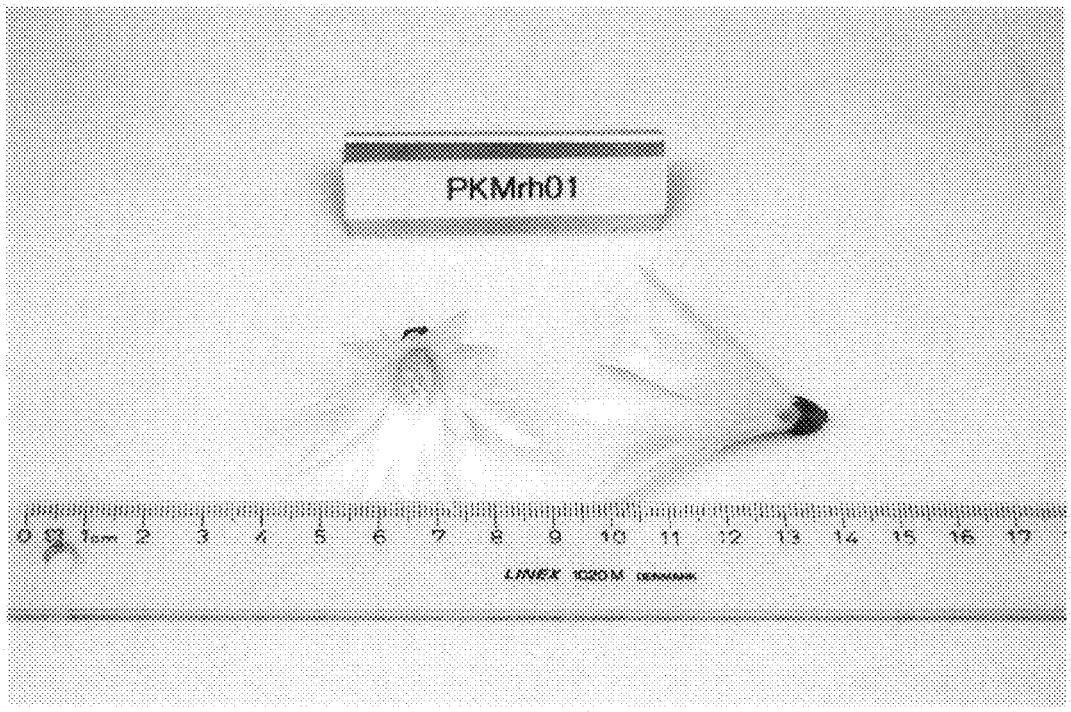
FIG. 4 shows a close-up top perspective view of a typical mature flower (on left) and a close-up side perspective view of a typical mature flower (on right) produced by 'PKMRH01'.
Figure 5:
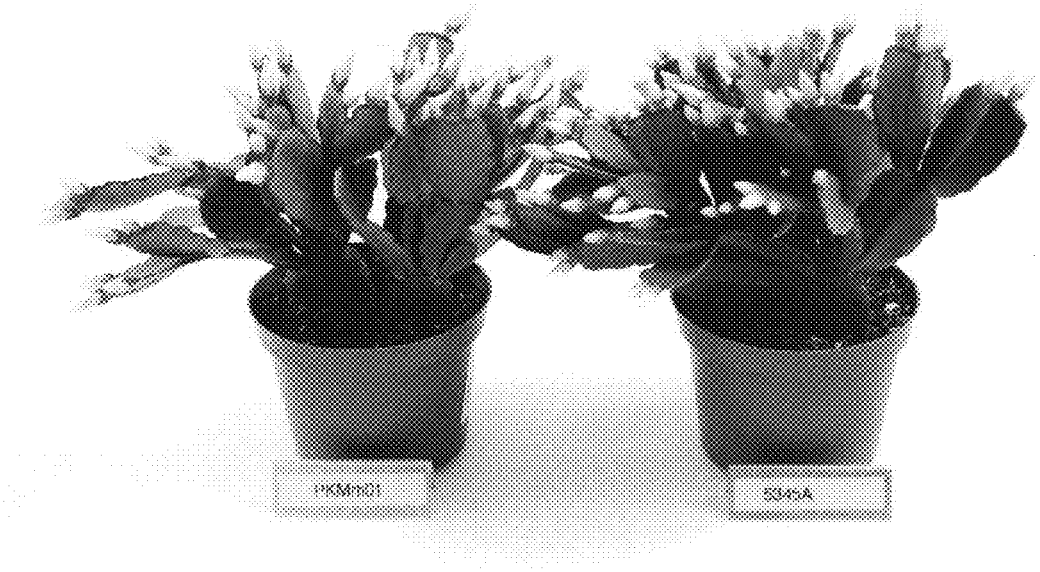
FIG. 5 shows a side perspective, comparison view of a typical mature plant of 'PKMRH01' with buds prior to flowering, grown in a 9.0 cm pots (on left), and a typical mature plant of the parental and most similar comparison cultivar Cebemma with buds prior to flowering, grown in a 9.0 cm pots (on right).
Figure 6:
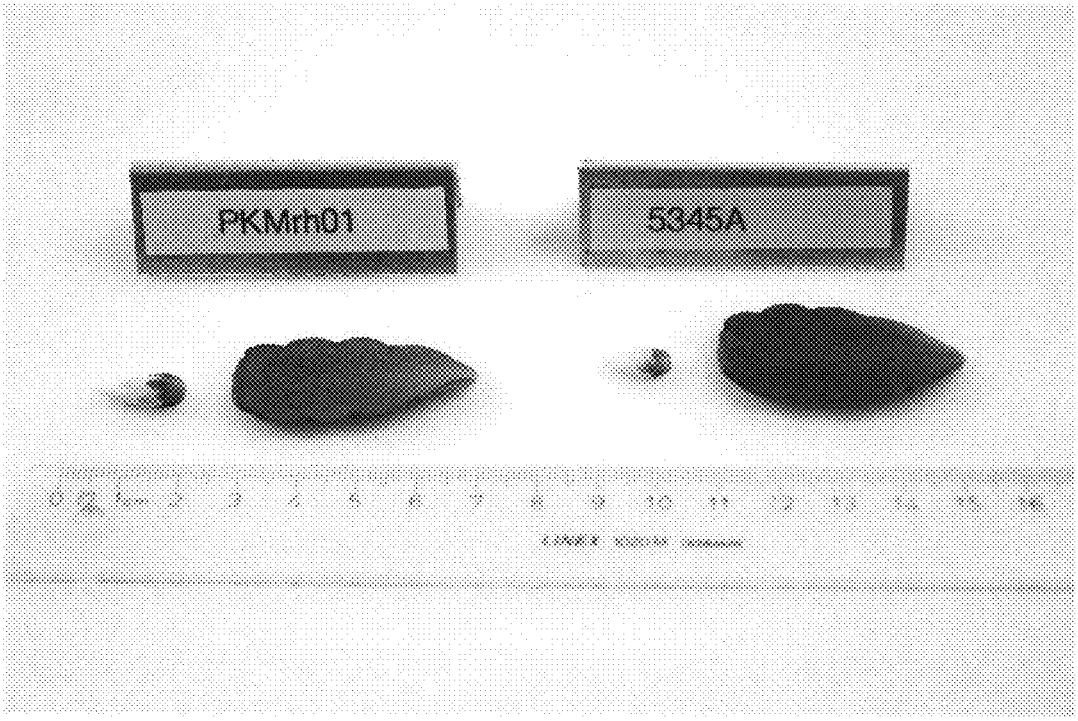
FIG. 6 shows a close-up perspective, comparison view of a typical bud just prior to flowering and a typical mature phylloclade of 'PKMRH01' (on left), and a typical bud just prior to flowering and a typical mature phylloclade of the parental and most similar comparison cultivar Cebemma (on right).
Figure 7:
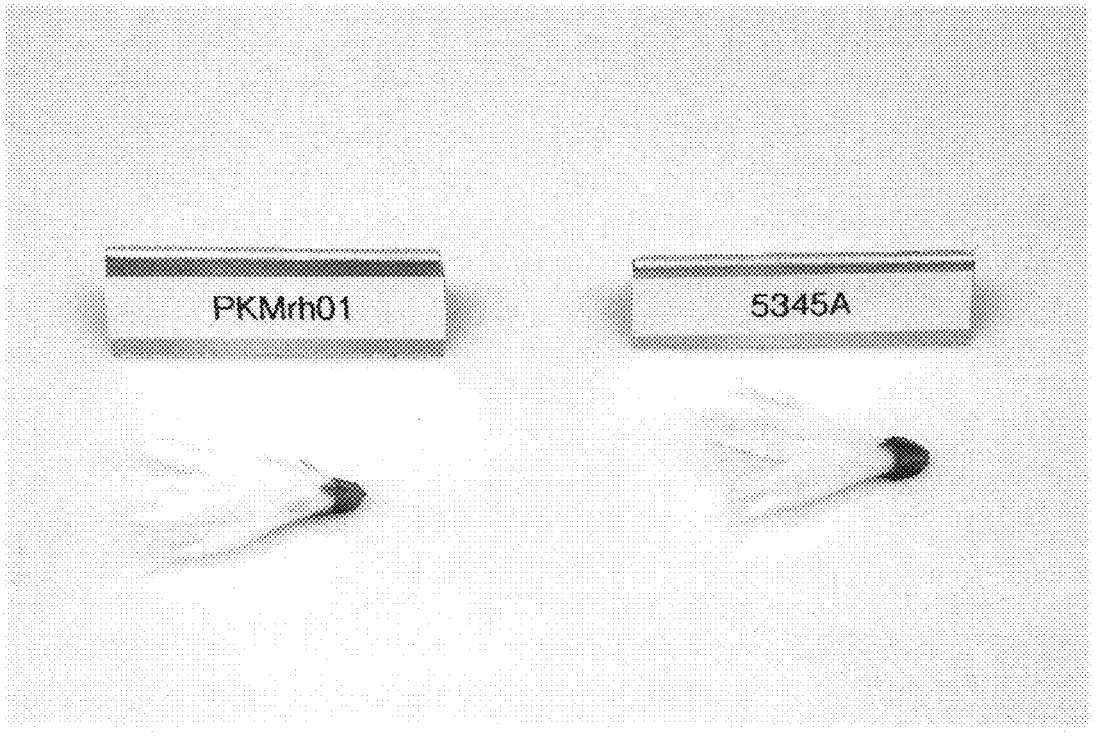
FIG. 7 shows a close-up side perspective, comparison view of a typical mature flower of 'PKMRH01' (on left), and a typical mature flower of the parental and most similar comparison cultivar Cebemma (on right).

The new *Rhipsalidopsis* cultivar 'PKMRH01' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMRH01' as grown in a glass-covered greenhouse in Fyn, Denmark, under conditions which closely approximate those generally used in commercial practice, where day temperatures in the greenhouse average 18° C. and night temperatures in the greenhouse average 16° C. Ambient light levels used while growing plants of 'PKMRH01' are +50Wm$^2$. Plants of 'PKMRH01' are thermo-photo-periodic and will develop buds and bloom best after short day treatments for 6-8 weeks and cool day/night temperatures of about 8° C. No growth retardants were used when growing plants of 'PKMRH01'.

The age of the 'PKMRH01' plants described is 11 months old and grown in 9.0 cm pots. The photographs and descriptions were taken during the winter season. Color references are made to The Royal Horticultural Society Colour Chart (R.H.S.), 4$^{th}$ edition, except where general colors of ordinary significance are used.

Classification:

*Botanical.*—*Rhipsalidopsis* Britton Et Rose.

*Common name.*—Easter Cactus or Spring Cactus.

Parentage:

*Female or seed parent.*—*Rhipsalidopsis* Britton Et Rose designated Cebemma (patented, U.S. Plant Pat. No. 14,588, European Union- Community Plant Variety Office Grant no.: 13,964).

*Male or pollen parent.*—*Rhipsalidopsis* Britton Et Rose designated '7302M' (unpatented).

Propagation: By phylloclade cuttings.

*Time and temperature to initiate roots.*—In a greenhouse, about 30 days at 18° C. to 21° C.

*Time and temperature to produce a rooted young plant.*—In a greenhouse, about 60 days at 18° C. to 21° C.

*Rooting habit and description.*—Fine, well-branched and yellow-white, RHS 159B in color.

Plant:

*Type.*—Perennial, Epiphyte.

*Growth habit.*—Initially erect and upright, becoming pendent as lateral branches lengthen.

*Branching habit.*—Freely branching, with two or three new phylloclades forming at the apical end of older phylloclades.

*Vigor.*—Slow growth rate.

*Crop time.*—After rooting, about 11 months are required to produce a finished flowering plant in a 9 cm pot.

*Size at maturity.*—Height (soil level to top of plant, including flowers): About 13 cm. Spread: About 20 cm to 22 cm.

Stem: None, older phylloclades may turn woody with age (several years).

Lateral Branches:

*Arrangement.*—Phylloclades form at the apex of older phylloclades to form branches.

*Quantity.*—About 9 to 12, when 3 phylloclade cuttings planted per pot.

*Length.*—Primary: About 3 cm to 4 cm (1 phylloclade). Secondary: About 12 cm (3 or 4 phylloclades).

*Width.*—About 2 cm to 3 cm.

*Aspect.*—Upright to arching (from basal phylloclade).

*Strength.*—Strong (from basal phylloclade).

*Appearance.*—Dull/matte.

*Pubescence.*—None.

Phylloclade:

*Arrangement.*—Single and sequential.

*Length.*—About 3 cm to 4 cm.

*Width.*—About 2 cm to 3 cm.

*Thickness.*—About 4 mm to 6 mm (at center vein of phylloclade).

*Overall shape.*—Oval.

*Apex shape.*—Truncate.

*Base shape.*—Rounded.

*Margin.*—Crenate.

*Texture.*—Glabrous, smooth.

*Pubescence.*—None.

*Color of immature phylloclade.*—Upper and lower surfaces: RHS 137C, yellow-green.

*Color of mature phylloclade.*—Upper and lower surfaces: RHS 137B, yellow-green.

*Venation.*—Pattern: Costate. Color: Upper and lower surfaces: RHS 137C, yellow-green.

Areole: Not true areole structure; tip of phylloclade is barbellate, 5 to 12 short hairs or bristles.

Inflorescence description:

*Arrangement and appearance.*—Single, double or triple sessile flowers born on apical end of phylloclades. Flowers are tubular, hose-in-hose perianth. When flowers are fully open, they form a right angle to the phylloclade. Flowers persistent.

*Natural flowering season.*—Flowering occurs from February to April (northern hemisphere), but can be changed depending on short day photo-treatments.

*Flowering response time.*—About 8 to 9 weeks after short day and vernalization.

*Rate of flowers opening.*—About 2 per week, depending on temperature and light.

*Flowering longevity* (*dependent on temperature and light conditions*).—About 5 to 6 days.

*Fragrance.*—None.

*Quantity of flowers per lateral branch.*—About 1 to 3.

*Quantity of buds per lateral branch.*—About 2.

*Quantity of flowers and buds per plant.*—About 30 to 45.

*Flower bud.*—Length: Ranging from 0 to 35 mm (before anthesis). Width: Ranging from 0 to 1 cm. Shape: Ovoid to lanceolatoid. Color: RHS NN155D, white, and RHS 62B, red-purple, near calyx lobe

*Flower.*—Type: Single, sessile. Shape: Tubular, hose-in-hose triple perianth. Aspect: Upright to vertical during development. Persistent or self-cleaning: Persistent.

*Corolla size.*—Height: About 3.5 cm to 4.5 cm (including ovary). Diameter: About 3 cm to 4 cm. Tube length: About 2 cm to 3 cm. Tube diameter: About 10 mm.

*Petals.*—Quantity: Apical Whorl: About 10; Basal whorl: About 5 to 7. Length: About 1.5 cm to 3.5 cm. Width: About 6 mm to 8 mm. Shape: Oval. Apex: Retuse. Base: Apical Whorl: Fused; Basal Whorl: Free. Margin: Entire. Appearance: Matte. Texture: Silky. Color (When Opening): Upper and lower surfaces: Petals: RHS NN155D, white. Tube: RHS NN155D, white. Color (When Fully Opened): Upper and lower surfaces: Petals: RHS NN155D, white. Tube: RHS NN155D, white. Color Fades to: RHS 158A, yellow-white.

*Petaloids.*—Arrangement: Free. Quantity: About 3 to 4. Length: About 10 mm to 12 mm. Width: About 5 mm to 7 mm. Shape: Oval. Apex: Acute. Base: Fused. Margin: Entire. Texture (both surfaces): Silky. Color (mature and immature): RHS 62B, red-purple.

*Sepals.*—Quantity: About 3. Length: About 3 mm to 5 mm. Width: About 2 mm. Shape: Ovate. Apex: Obtuse to rounded. Base: Truncate. Margin: Grooved. Texture (both surfaces): Glabrous, Silky. Color (Immature and Mature): RHS 67A, red-purple.

Reproductive organs:

*Androecium.*—Stamen: Quantity: Many (about 50 to 70), polyandrous, incurved. Some filaments fused to perianth tube (connate). Length: About 17 mm. Color: RHS NN155D. Anther: Shape: Ovoid. Length: About 1 mm. Color: RHS 16A, yellow-orange. Filament: Length: About 15 to 16 mm. Color: RHS NN155D, white. Pollen: Amount: Abundant. Color: RHS 16A, yellow-orange.

*Gynoecium.*—Pistil: Quantity: 1. Shape: Claw-like. Length: About 15 mm. Stigma: Shape: Ovoid. Color: RHS 16D, yellow-orange. Style: Length: About 15 mm. Color: RHS NN155D, white. Ovary: Shape: Angular. Length: About 5 mm. Width: About 2 mm to 3 mm. Color: RHS NN155D, white Seeds/fruit: None observed.

Disease/pest resistance: No test for disease/pest resistance have been performed yet.

Disease/pest susceptibilty: No test for disease/pest resistance have been performed yet.

Temperature tolerance: Tolerant to a low temperature of about 2° C. and to a high temperature about 40° C. Good tolerance to drought.

I claim:

1. A new and distinct *Rhipsalidopsis* plant named 'PKMRH01', as illustrated and described herein.

* * * * *